United States Patent
Arai

(10) Patent No.: US 10,018,976 B2
(45) Date of Patent: Jul. 10, 2018

(54) METHOD AND APPARATUS FOR DETERMINING AN OPTIMAL SEPARATION MEDIUM FOR ELECTROPHORESIS

(71) Applicant: SHIMADZU CORPORATION, Kyoto-shi, Kyoto (JP)

(72) Inventor: Akihiro Arai, Kyoto (JP)

(73) Assignee: SHIMADZU CORPORATION, Kyoto-shi, Kyoto (JP)

(*) Notice: Subject to any disclaimer, the term of this patent is extended or adjusted under 35 U.S.C. 154(b) by 459 days.

(21) Appl. No.: 14/609,762

(22) Filed: Jan. 30, 2015

(65) Prior Publication Data

US 2016/0223485 A1 Aug. 4, 2016

(51) Int. Cl.
*G01N 27/447* (2006.01)
*G05B 15/02* (2006.01)
*C12N 15/10* (2006.01)

(52) U.S. Cl.
CPC .......... *G05B 15/02* (2013.01); *C12N 15/101* (2013.01); *G01N 27/44747* (2013.01)

(58) Field of Classification Search
CPC ............................................... G01N 27/44747
See application file for complete search history.

(56) References Cited

U.S. PATENT DOCUMENTS 6,770,698 B1 * 8/2004 Chu .................... C08F 271/00
524/458

OTHER PUBLICATIONS

Chiari et al., "Movement of DNA fragments during capillary zone electrophoresis in liquid polyacrylamide," Journal of Chromatography A, 652 (1993) 21-39.*
Liu et al., "Prediction of DNA Separation by Capillary Electrophoresis with Polymer Additives," Journal of Chromatographic Science, vol. 49, Apr. 2011.*
Guillaume et al., Chemometric method to optimize chiral separation of imidazole derivatives by capillary electrophoresis, Talanta 50 (1999) 533-540 (Year: 1999).*

* cited by examiner

*Primary Examiner* — Alexander S Noguerola
(74) *Attorney, Agent, or Firm* — Sughrue Mion, PLLC

(57) ABSTRACT

Resolution maps for size segments to which the size range of the measurement sample extends are retrieved. A high resolution region is extracted from the retrieved size segment resolution maps. After extracting the high resolution regions, the resolution maps are overlaid, the region where the high resolution regions overlap is taken as a high resolution overlap region, and the composition of a point within that high resolution overlap region is determined as the composition of a separation medium appropriate for separation of the measurement sample. The separation media A, B and C are mixed so as to achieve the determined composition, thereby preparing a mixed separation medium to be used for separation of the measurement sample.

19 Claims, 13 Drawing Sheets

GENERATION OF RESOLUTION MAP

| Size segment \ Reference location | 1 | 2 | 3 | 4 | 5 |
|---|---|---|---|---|---|
| 72-118 | 9.63868 | 7.734627 | 2.192945 | 6.01904 | 1.970278 |
| 118-194 | 13.33847 | 12.27872 | 4.353344 | 9.303387 | 3.589017 |
| 194-234 | 5.060106 | 5.483591 | 1.917996 | 4.061837 | 1.738028 |
| 234-271 | 5.066216 | 5.3818 | 1.947604 | 4.07305 | 1.594796 |
| 271-281 | 0.846274 | 1.112571 | 0 | 0.754983 | 0 |
| 281-310 | 2.964697 | 3.5829 | 1.719668 | 2.524548 | 1.379989 |
| 310-603 | 15.31197 | 18.58491 | 9.944998 | 14.83445 | 8.564878 |
| 603-872 | 4.169142 | 4.670113 | 4.817909 | 5.827217 | 4.52763 |
| 872-1078 | 1.5645 | 1.219249 | 2.043077 | 0.858335 | 2.038095 |
| 1078-1353 | 1.124286 | 0.733159 | 1.197627 | 0.282784 | 1.372352 |

| Size segment \ Reference location | 6 | 7 | 8 | 9 | 10 |
|---|---|---|---|---|---|
| 72-118 | 8.1947 | 6.735697 | 8.884325 | 5.85694 | 5.193564 |
| 118-194 | 11.86823 | 10.00651 | 11.45834 | 9.065834 | 8.059218 |
| 194-234 | 5.079405 | 4.474399 | 4.670254 | 4.144022 | 3.686953 |
| 234-271 | 4.99755 | 4.441095 | 4.300838 | 4.063738 | 3.736684 |
| 271-281 | 1.078663 | 0.984071 | 0.923447 | 0.939161 | 0.85595 |
| 281-310 | 3.282194 | 3.078728 | 2.831864 | 2.894978 | 2.777606 |
| 310-603 | 17.35283 | 17.76533 | 13.86859 | 15.35154 | 16.78124 |
| 603-872 | 4.847813 | 6.018994 | 4.163609 | 5.184884 | 6.69915 |
| 872-1078 | 1.390292 | 1.950627 | 1.441081 | 1.593538 | 2.281662 |
| 1078-1353 | 0.954247 | 1.333582 | 1.179707 | 0.982207 | 1.382715 |

METHOD AND APPARATUS FOR DETERMINING AN OPTIMAL SEPARATION MEDIUM FOR ELECTROPHORESIS

TECHNICAL FIELD

The present invention relates to microchip electrophoretic analysis wherein, using a microfluidic device containing a separation channel inside a plate-shape member, a sample such as DNA, RNA or protein which has been introduced into one end of the separation channel is analyzed after separating it by causing the sample to migrate toward the other end of the separation channel by means of voltage applied between the two ends of the separation channel. Specifically, the present invention relates to a method of determining the composition of the separation medium to be filled into the separation channel for electrophoretic analysis, a program for determining the composition of the separation medium, a recording medium which stores the program, a separation medium preparation device which automatically determines and adjusts the composition of the separation medium, and an electrophoresis method using the prepared separation medium.

BACKGROUND ART

For separation and analysis of DNA, RNA and proteins using a microfluidic device, it is necessary to fill the fine channel thereof with a separation medium for changing the mobility according to the size of the molecule. Water soluble polymer solution is commonly used as a separation medium based on ease of filling into the channel and ease of replacement. Furthermore, it is common to perform optimization of the molecular weight (degree of polymerization) and concentration of the water soluble polymer solution according to the molecular weight of the sample to be analyzed. For example, if the sample is DNA of short chain length (hereinafter referred to as size), the molecular weight of the water soluble polymer solution would be reduced and its concentration increased, and if the sample is DNA of long chain length, the molecular weight of the water soluble polymer solution would be increased and its concentration reduced.

In this way, since the optimal conditions of the separation medium differ depending on the molecular weight of the sample to be analyzed, it has been necessary to prepare multiple types of water soluble polymers according to the application, and to have the user correctly select the water soluble polymer appropriate for the sample to be analyzed. For example, in the case of dsDNA fragment analysis, in order to achieve separation across a wide chain length range (also called size range) of 25 bp to 12000 bp, it was necessary to prepare at least three types of water soluble polymers. With just one type of water soluble polymer, the size range across which a high resolution can be obtained is limited, so it was difficult to achieve separation of samples of different size ranges at a high precision with a single type of water soluble polymer.

SUMMARY OF THE INVENTION

Problem to be Solved by the Invention

As described above, it is difficult to perform the separation of a sample having a wide size range or the separation of multiple types of samples of different size ranges with just a single type of separation medium. Thus, when the separation of multiple samples of different size ranges is to be performed, there is the problem that each time, the user needs to change the separation medium to one appropriate for the size range of the sample, making the operation complicated and leading to errors in selection of the separation medium.

Starting in the early 1990s, many cases have been reported where cellulose derivatives were used as a separation medium for DNA fragments. Examples of the cellulose derivatives include methyl cellulose, hydroxyethyl cellulose, hydroxypropyl cellulose, hydroxypropyl methyl cellulose and the like. All of these make it possible to adjust the size characteristics of separation of DNA fragments by changing the mesh size of the polymer network by adjusting the molecular weight, concentration and pH.

It is thus the object of the present invention to make it possible to easily prepare separation media appropriate for the size range of the sample.

Means for Solving the Problem

In the method of determining the composition of a separation medium for electrophoresis according to the present invention, the separation medium to be used for electrophoretic analysis of a measurement sample is determined by performing the following steps in the indicated sequence:

a resolution map preparation step wherein a resolution map, which shows, based on the location on its surface, the relationship between the composition of a mixed separation medium prepared by mixing multiple types of separation media and the resolution obtained by performing analysis using a separation medium of that composition, is prepared for each of multiple contiguous size segments;

a high resolution region extraction step wherein a high resolution region having the resolution necessary for separation of the measurement sample is extracted from the resolution map of the size segment to which the size range of the measurement sample extends; and a mixed separation medium composition determination step wherein a point within the high resolution region is selected as a high resolution point and the composition of that high resolution point is determined as the composition of the mixed separation medium to be used for electrophoretic analysis of the measurement sample.

The program for determining the composition of a separation medium for electrophoresis according to the present invention is configured so as to determine the composition of the separation medium to be used for electrophoretic analysis of a measurement sample by executing the following steps in the indicated sequence, using resolution map information comprising resolution maps, which show the relationship between the composition of a mixed separation medium prepared by mixing multiple types of separation media and the resolution obtained by performing analysis using a separation medium of that composition based on location on the surface thereof, and are prepared for each of multiple contiguous size segments:

a high resolution region extraction step wherein a high resolution region having the resolution necessary for separation of the measurement sample is extracted from the resolution map of the size segment to which the size range of the measurement sample extends; and a mixed separation medium composition determination step wherein a point within the high resolution region is selected as a high resolution point and the composition of that high resolution point is determined as the composition of the mixed separation medium to be used for electrophoretic analysis of the measurement sample.

The recording medium according to the present invention is used on a computer and stores resolution map information comprising resolution maps, which show the relationship between the composition of a mixed separation medium prepared by mixing multiple types of separation media and the resolution obtained by performing analysis using a separation medium of that composition based on location on the surface thereof, and are prepared for each of multiple contiguous size segments; and the composition determination program described in the present invention.

The separation medium preparation device according to the present invention comprises: a medium liquid feed mechanism which individually feeds multiple types of separation medium liquids; a mixer for mixing the separation medium liquids fed by the medium liquid feed mechanism; a resolution map information storage unit which stores resolution map information comprising resolution maps, which show the relationship between the composition of a mixed separation medium prepared by mixing multiple types of separation media and the resolution obtained by performing analysis using a separation medium of that composition based on location on the surface thereof, and are prepared for each of multiple contiguous size segments; the program for determining the composition of a separation medium for electrophoresis of the present invention; and a control unit comprising a separation medium composition determination means which determines the composition of a separation medium by means of the composition determination program on the basis of a set measurement sample size range, and a separation medium preparation means which controls the operation of the medium liquid feed mechanism to prepare a mixed separation medium so as to have the determined composition.

The electrophoresis method according to the present invention comprises: a step of filling a separation channel of an electrophoresis chip with a separation medium of a composition determined by the composition determination method of the present invention; a step of dispensing a sample into a sample reservoir provided at one end of the separation channel; and a step of causing the sample to migrate through the separation channel by applying a voltage between the two ends of the separation channel and detecting migrating components of the sample at a predetermined location of the separation channel.

Effect of the Invention

According to the method of determining the composition of a separation medium for electrophoresis of the present invention, a resolution map which shows, based on the location on its surface, the relationship between the composition of a mixed separation medium prepared by mixing multiple types of separation media and the resolution obtained by performing analysis using a separation medium of that composition, is prepared for each of multiple contiguous size segments; a high resolution region having the resolution necessary for separation of the measurement sample is extracted from the resolution map of the size segment to which the size range of the measurement sample extends; and the composition of a high resolution point within that high resolution region is determined as the composition of the mixed separation medium to be used for electrophoretic analysis of the measurement sample, thus making it possible to easily obtain a mixed separation medium having separation characteristics appropriate for separation of a measurement sample.

The composition determination program of the present invention is configured so as to determine the composition of the separation medium to be used for electrophoretic analysis of a measurement sample by using resolution map information comprising resolution maps, which show the relationship between the composition of a separation medium and resolution based on location on the surface thereof and are prepared for each of multiple contiguous size segments; extracting a high resolution region having the resolution necessary for separation of the measurement sample from the resolution map of the size segment to which the size range of the measurement sample extends; and determining the composition of a high resolution point within the high resolution region as the composition of the mixed separation medium to be used for electrophoretic analysis of the measurement sample, thus making it possible to rapidly determine the composition of a mixed separation medium appropriate for separation of a measurement sample.

The recording medium of the present invention stores resolution map information and the composition determination program described in the present invention, thus making it possible to install the composition determination program on a computer to be used for electrophoretic analysis. The composition of a separation medium appropriate for electrophoretic analysis of the measurement sample is thereby automatically determined on the computer on which the composition determination program has been installed.

The separation medium preparation device of the present invention comprises a medium liquid feed mechanism, a mixer, a resolution map information storage unit, the composition determination program of the present invention and a control unit, wherein the control unit comprises a separation medium composition determination means which determines the composition of a separation medium by means of the composition determination program on the basis of a set measurement sample size range, and a separation medium preparation means which controls the operation of the medium liquid feed mechanism to prepare a mixed separation medium so as to have the determined composition, thus making it possible to automatically perform determination of the composition of a separation medium appropriate for that size range and preparation of a separation medium of that composition just by having the user set the size range of the measurement sample on the device.

With the electrophoresis method of the present invention, electrophoresis of a sample is performed using a separation medium prepared to a composition determined by the composition determination method of the present invention, thus making it possible to achieve high separation and perform high precision analysis based on the separation characteristics of a separation medium appropriate for the size range of a sample.

DETAILED DESCRIPTION OF THE EXEMPLARY EMBODIMENTS

Figure 1:
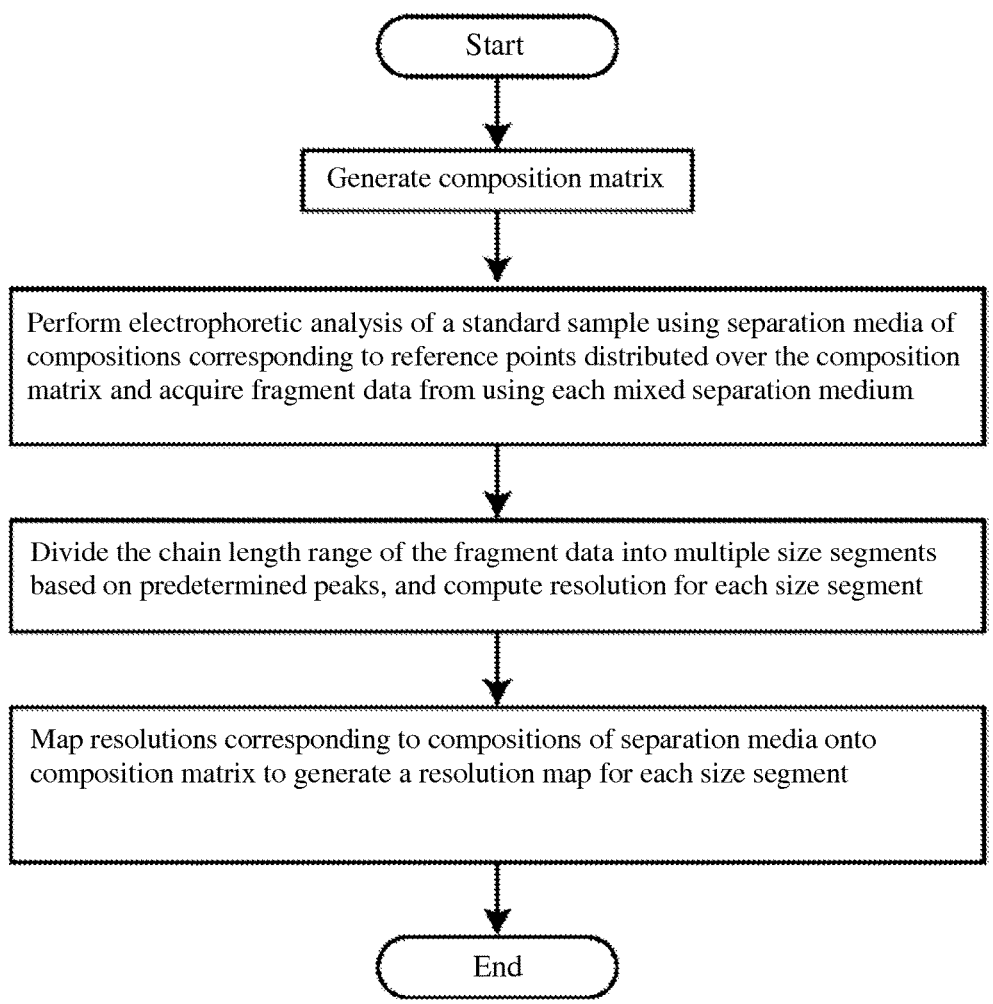
FIG. 1 is a flow chart illustrating the resolution map generation procedure in one embodiment example of a separation medium preparation method.

In the separation medium composition determination method and composition determination program of the present invention, when the size range of the measurement sample extends over multiple size segments, it is preferable to extract a high resolution region from each of the resolution maps of those size segments and extract the region contained in all of those high resolution regions as a high resolution overlap region in the high resolution region extraction step, and to select a point within the high resolution overlap region as the high resolution point and determine the composition of that high resolution point as the composition of the mixed separation medium to be used for electrophoretic analysis of the measurement sample. In this way, when the size range of the measurement sample is broad, it is possible to determine the composition of a separation medium exhibiting high separation characteristics in all regions of the broad size range.

In the separation medium preparation device of the present invention, the medium liquid feed mechanism may comprise a syringe pump for feeding each separation medium liquid; a static mixer whereof one end is connected to all of the syringe pumps, and which mixes the separation medium liquids fed by the syringe pumps; and a probe which is connected to the other end of the static mixer and dispenses the mixed separation medium prepared by mixing in the static mixer. This makes it possible to prepare a mixed separation medium of a composition appropriate for the size range of the measurement sample in the static mixer and fill the prepared mixed separation medium into the separation channels of the electrophoresis chip from the end of the probe, allowing the device to also function as a separation medium filling device.

The resolution map information and composition determination program possessed by the separation medium preparation device of the present invention may be inputted into the device via the recording medium of the present invention on which these have been stored.

An embodiment example of the method of preparing a separation medium to be used for electrophoretic analysis will be described.

In the preparation method of this embodiment example, three types of water soluble polymers (separation media) A, B and C are used, and the mixing ratio of these separation media is adjusted according to the size range of the measurement sample to prepare a separation medium having the desired separation characteristics appropriate for separation of the measurement sample. The mixing ratio of the separation media is determined using resolution maps prepared based on the separation characteristics of each separation medium A, B and C.

While three types of separation media are used in this embodiment example, the preparation method of the present invention is not limited thereto, it being also possible to prepare a mixed separation medium having the desired separation characteristics by mixing two separation media or four or more separation media. In the following, a separation medium prepared by mixing multiple types of water soluble polymers will be referred to as "mixed separation medium".

First, the method of generating resolution maps to be used during preparation of the mixed separation medium will be described using the flow chart of FIG. 1 and the drawings of FIG. 2 through FIG. 5.

In this embodiment example, three types of hydroxyethyl cellulose (hereinafter, HEC) will be used as the separation media A, B and C. Separation medium A is s 2% solution of HEC (product made by Sigma-Aldrich Co., Mw (weight average molecular weight)=250000), separation medium B is a 0.4% solution of HEC (product made by Sigma-Aldrich Co., Mv (viscosity average molecular weight)=720000), and separation medium C is a 0.2% solution of HEC (product made by Sigma-Aldrich Co., Mv=1300000).

Figures 4, 5:
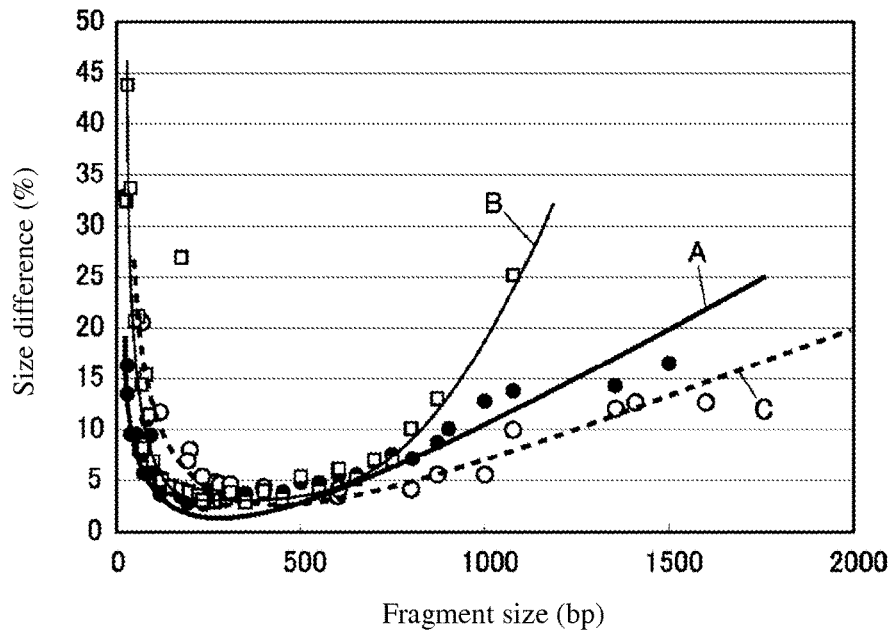
FIG. 4 is a graph illustrating the separation characteristics of each separation medium used in the same embodiment example.
FIG. 5 is a table showing the resolution for each size segment at each reference location of the composition matrix of the same embodiment example.

The separation characteristics of separation media A, B and C are shown in FIG. 4. FIG. 4 graphs the separation characteristics for each fragment size, determined through calculation, using fragment analysis data obtained by performing electrophoretic separation of a standard sample (ΦX174-HaeIII digest) using each of the separation media A, B and C. In this calculation, using formula (1), a resolution (Rs) was defined assuming that the width and height of two adjacent peaks (fragments) are the same, and Rs≥1 was taken as the criterion for whether or not separation had taken place. Furthermore, the size resolution (%) of each size segment was found based on (size resolution [bp]/size of one peak [bp])=(size difference of two adjacent peaks

[bp])/Rs/(size of one peak [bp]) (%). In this graph, size difference signifies the difference of fragment size (chain length) in which two peaks necessary for Rs to be equal to 1 appear.

$$R_S = 2 \times \frac{t_2 - t_1}{w_{h,1} + w_{h,2}} = \sqrt{2\ln(2)} \times \frac{t_2 - t_1}{w_{h,1} + w_{h,2}} \quad (1)$$

Here, t is migration time, $W_b$ is baseline peak width, and $W_h$ is peak width at ½ peak height.

As shown in FIG. 4, the three separation media A, B and C have been optimized to a concentration that gives the best separation between fragments of the standard sample (ΦX174-Hae III digest). However, if the resolution criterion is stipulated as being 10% or less of the size difference, separation medium A lacks resolution in the long chain side region (region of fragment size of 1000 bp or greater), separation medium B lacks resolution in the long chain side region (region of fragment size of 800 bp or greater), and separation medium C lacks resolution in the short chain side region (region of fragment size of 200 bp or less), so it is not possible to support separation of a broad size range with one of these separation media A, B or C alone. Thus, a mixed separation medium appropriate for the size range of the measurement sample will be prepared by mixing these three types of separation media A, B and C.

Figure 3:
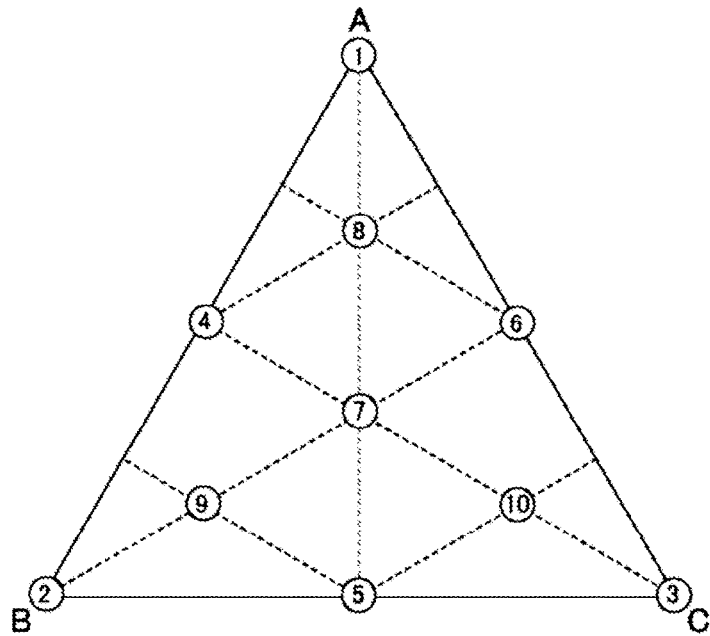
FIG. 3 is a drawing illustrating an example of a composition matrix when using three types of separation media.

First, as shown in FIG. 3, a composition matrix is generated wherein reference points 1 through 10 are substantially uniformly distributed according to the mixing ratio (composition) of the three types of separation media A, B and C. Each reference point 1 through 10 in the composition matrix has a composition corresponding to its respective location.

The composition (mixing ratio) of each of the reference points 1 through 10 is reference point 1: (A/B/C)=(1/0/0); reference point 2 (A/B/C)=(0/1/0); reference point 3: (A/B/C)=(0/0/1); reference point 4: (A/B/C)=(0.5/0.5/0); reference point 5: (A/B/C)=(0/0.5/0.5); reference point 6: (A/B/C)=(0.5/0/0.5); reference point 7: (A/B/C)=(0.33/0.33/0.33); reference point 8: (A/B/C)=(0.67/0.17/0.17); reference point 9: (A/B/C)=(0.17/0.67/0.17); reference point 10: (A/B/C)=(0.17/0.17/0.67).

Next, using the mixed separation media having the compositions of each reference point 1 through 10, electrophoretic separation of a standard sample (ΦX174-Hae III digest) was performed, the results were divided into multiple size segments based on adjacent fragments appearing in the fragment analysis data, and the resolution Rs for each size segment was determined using the aforementioned formula (1). FIG. 5 shows the resolution Rs for each segment (size segment) delimited by the fragments in the fragment analysis data as a table.

Based on the data of FIG. 5, the resolution Rs of each reference location 1 through 10 in each size segment was mapped onto the composition matrix to generate resolution maps for each size segment, as shown in FIG. 6 through FIG. 9. By extracting a region of a set resolution or higher from these resolution maps, it is possible to determine the composition of the separation medium having a set resolution or higher in the respective size segment. Resolution maps of this sort are generated for all of the size segments and are stored in a storage unit provided inside the device or in a storage unit of a personal computer connected to the device, and are retrieved and used when determining the composition of the mixed separation medium.

Figure 2:
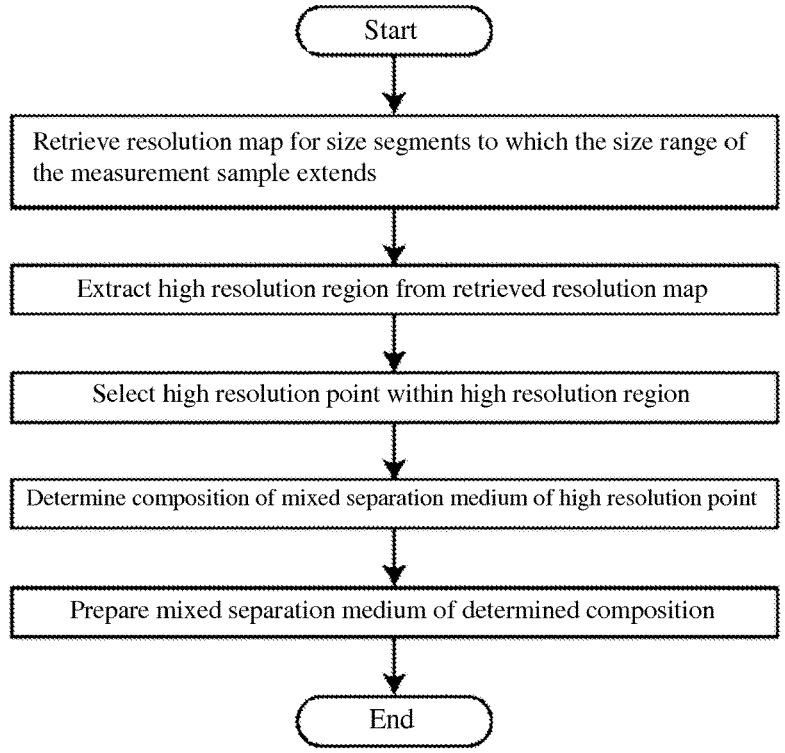
FIG. 2 is a flow chart illustrating the mixed separation medium preparation procedure in an embodiment example of a separation medium preparation method.

The method of preparing a mixed separation medium will be described using the flow chart of FIG. 2 and the drawings of FIG. 6 through FIG. 12.

A resolution map for the size segment to which the size range of the measurement sample extends is retrieved. In this example, the preparation of a mixed separation medium having high resolution over the entire size range (72 bp through 1353 bp (see FIG. 5)) will be described. A threshold value (for example, Rs>1) required for separation of the measurement sample is defined for each resolution map of all the size segments, and a high resolution region exceeding that threshold value is extracted from each resolution map.

Regarding the size segments 72 bp-118 bp, 118 bp-194 bp, 194 bp-234 bp, 234 bp 271 bp, 310 bp-603 bp and 603 bp-872 bp, high resolution was indicated for all the reference points 1 through 10, so for these regions, the entire map is extracted as the high resolution region.

Figure 6:
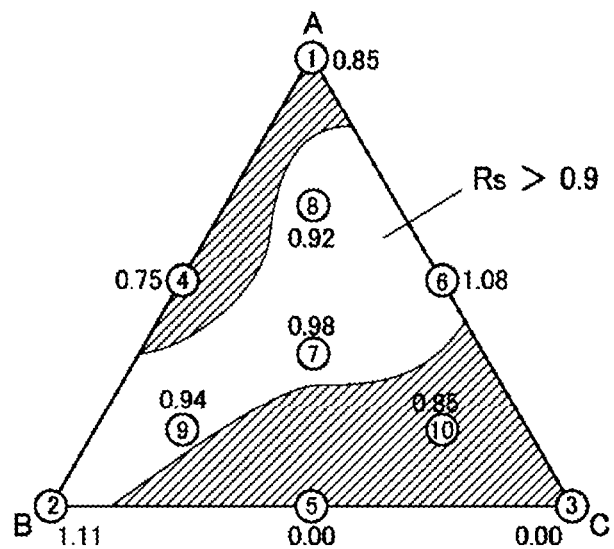
FIG. 6 is a resolution map for size segments 271-281 in the same embodiment example.

For the size segment of 271 bp-281 bp, as shown in FIG. 6, using a threshold value of 0.9, the region of Rs>0.9 is extracted as the high resolution region.

Figure 7:
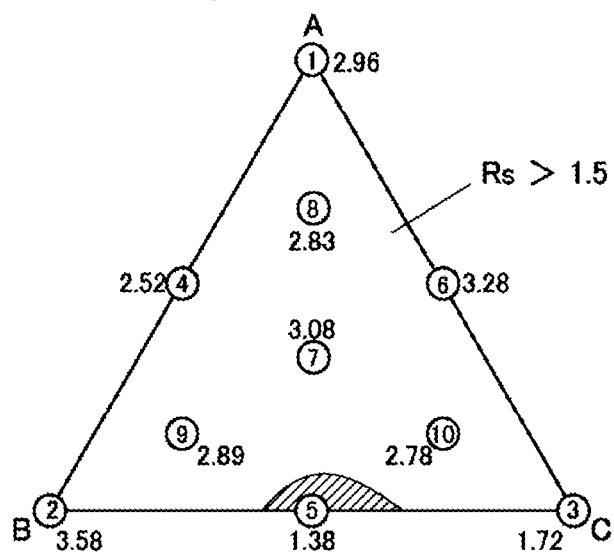
FIG. 7 is a resolution map for size segments 281-310 in the same embodiment example.

For the size segment of 281 bp-310 bp, as shown in FIG. 7, using a threshold value of 1.5, the region of Rs>1.5 is extracted as the high resolution region. It should be noted that adequate resolution will be obtained so long as Rs≥1, so it is also possible to exact the entire region as the high resolution region given that Rs>1.

Figure 8:
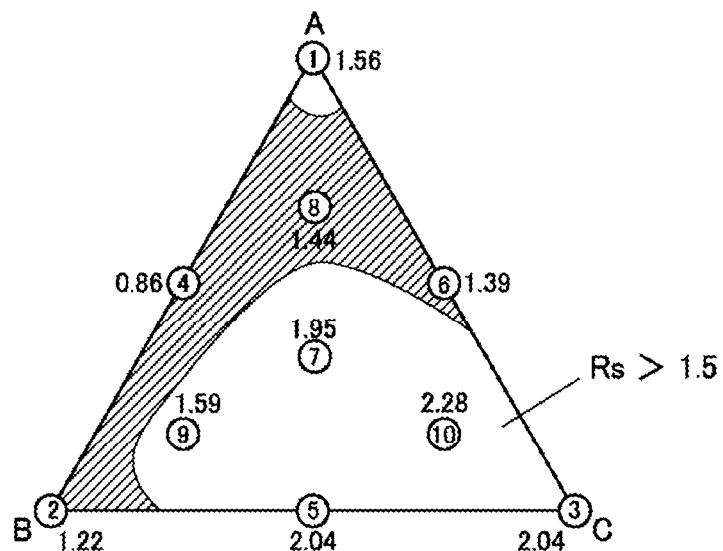
FIG. 8 is a resolution map for size segments 282-1078 in the same embodiment example.

For the size segment of 872 bp-1078 bp, as shown in FIG. 8, using a threshold value of 1.5, the region of Rs>1.5 is extracted as the high resolution region. It should be noted that adequate resolution will be obtained so long as Rs≥1, so it is also possible to use Rs>1 as the condition for the high resolution region.

Figure 9:
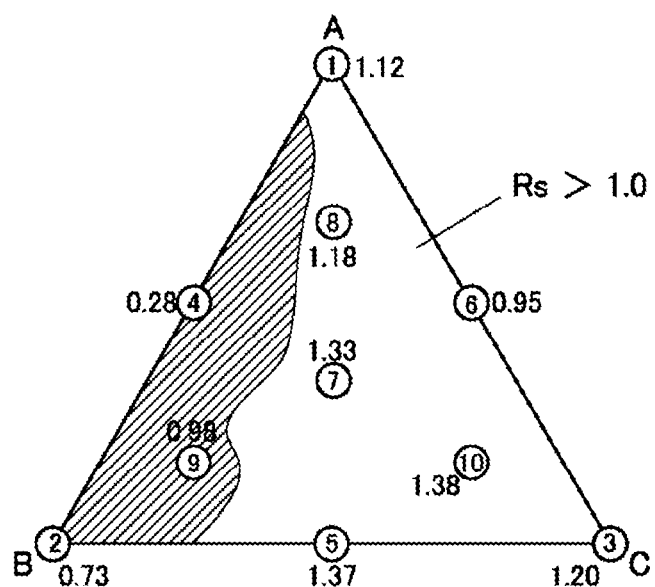
FIG. 9 is a resolution map for size segments 1078-1353 in the same embodiment example.

For the size segment of 1078 bp-1353 bp, as shown in FIG. 9, using a threshold value of 1, the region of Rs>1 is extracted as the high resolution region.

Figure 10:
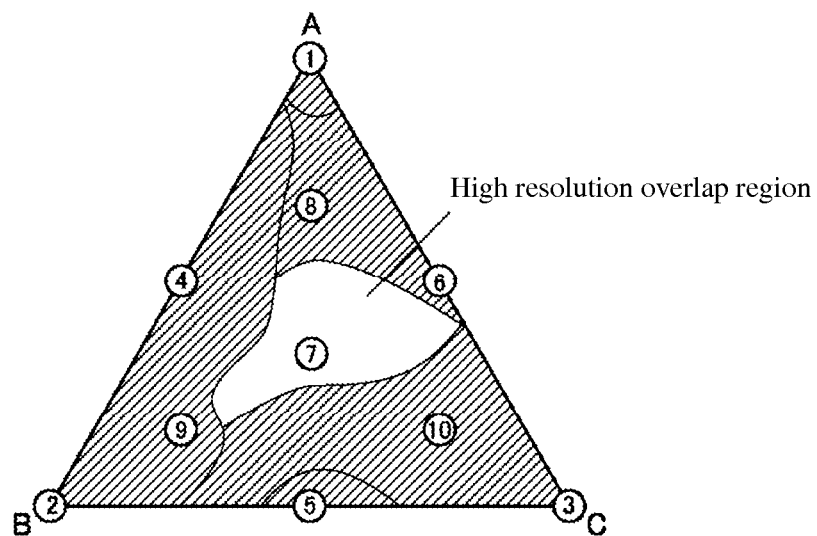
FIG. 10 is a drawing in which the resolution maps of FIGS. 6 through 9 have been overlaid.

As shown in FIG. 10, after extracting the high resolution region in each retrieved size segment, the resolution maps for each of the size segments are overlaid and the region where the high resolution regions overlap is taken as the high resolution overlap region. The region which has not been hatched is the high resolution overlap region. In this high resolution overlap region, for example, the point with the highest resolution is selected as the high resolution point, and the composition of that high resolution point is determined as the composition of the mixed separation medium. Then, based on the composition of the high resolution point, A, B and C are mixed to prepare a mixed separation medium. By using this mixed separation medium, it is possible to achieve Rs>0.9 in the 72 bp to 1353 bp fragment size range.

Figure 11:
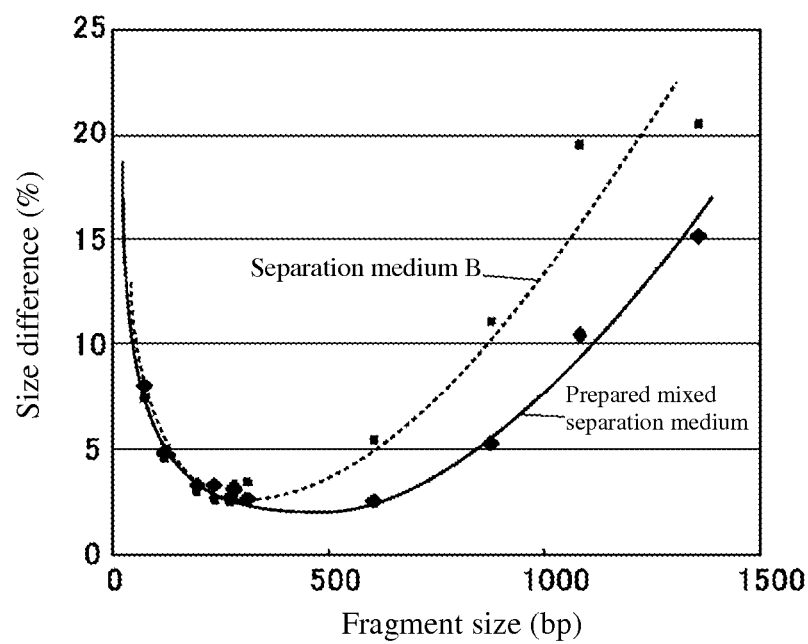
FIG. 11 is a graph illustrating the separation characteristics of a mixed separation medium prepared by the preparation method of the same embodiment example and of separation medium B alone.

(A/B/C/)=(0.4/0.2/0.4) can be mentioned as a mixing ratio corresponding to a point within the aforementioned high resolution region. The size resolution (Rs=1) when performing electrophoretic analysis of the standard sample (ΦX174-Hae III digest) using a mixed separation medium prepared at this mixing ratio is shown in FIG. 11. When using separation medium B alone, the range of fragment sizes for which the size difference is 10% or less is 80 bp to 800 bp, while when using a mixed separation medium prepared at a mixing ratio of (A/B/C)=(0.4/0.2/0.4), the range of fragment sizes for which the size difference is 10% or less expands, becoming 50 bp to 1200 bp.

The mixing ratios of mixed separation medium based on three types of separation media D, E and F, optimized for the size ranges of 25 bp to 500 bp, 100 bp to 1000 bp, 100 bp to 2500 bp and 100 bp to 12000 bp using the above-described separation medium preparation method, are shown below. Here, separation medium D is a 2% solution of HEC (product of Sigma-Aldrich Co., Mw (weight average molecular weight)=250000), separation medium E is a 0.36% solution of HEC (product of Polysciences Co., Mw=720000 (Mn (number average molecular weight)= 105000)), and separation medium F is a 0.18% solution of HEC (product of Polysciences Co., Mw=1000000 (Mn=160000)).

25 bp to 500 bp: (D/E/F)=(1/0/0)
100 bp to 1000 bp: (D/E/F)=(0.2/0.4/0.4)
100 bp to 2500 bp: (D/E/F)=(0/0.5/0.5)
100 bp to 12000 bp: (D/E/F)=(0/0/1)

Figure 12:
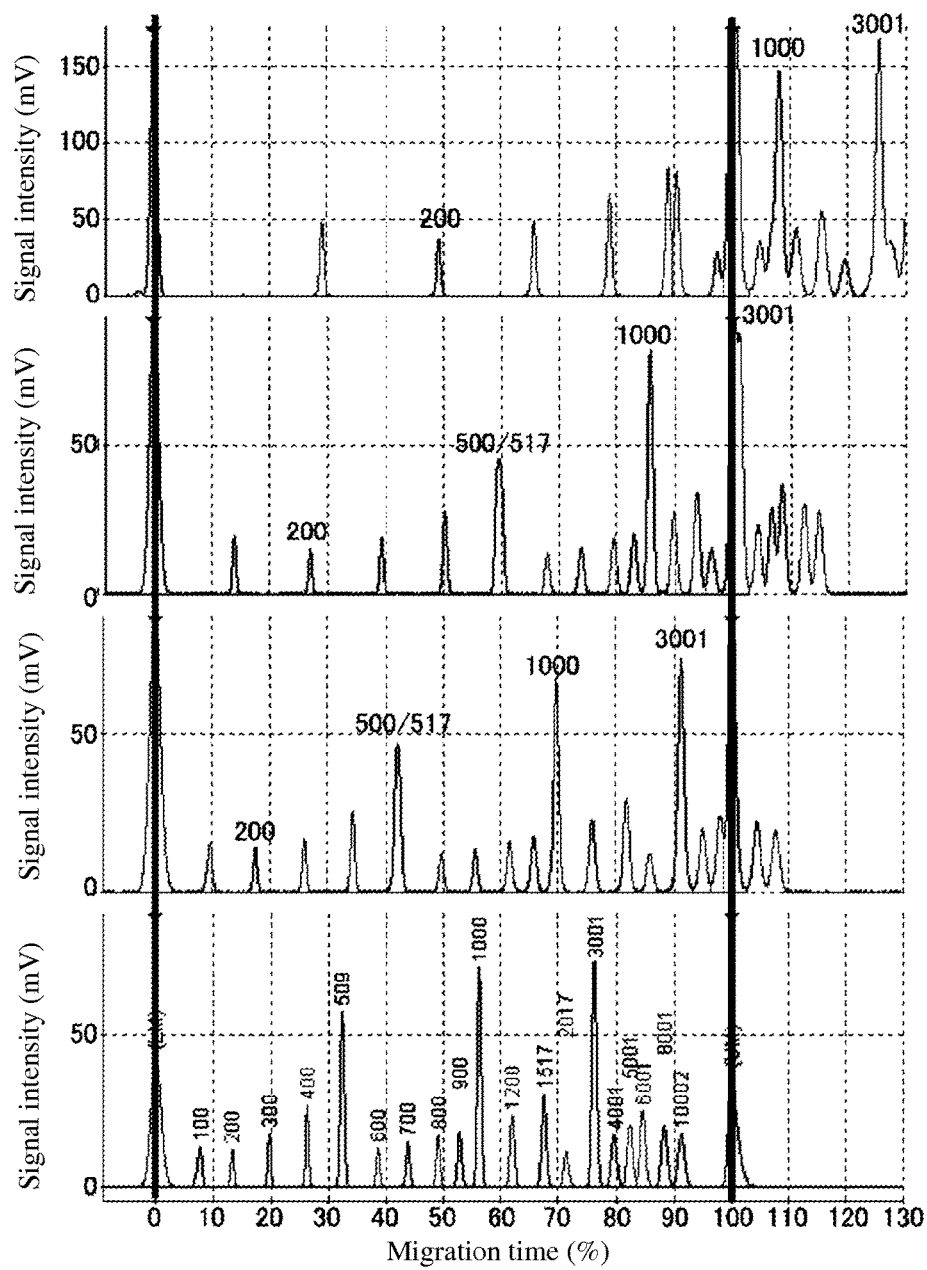
FIG. 12 is fragment analysis data from using the mixed separation medium prepared by the preparation method of the same embodiment example.

FIG. 12 is fragment analysis data obtained by performing electrophoresis on 2-Log DNA ladder (made by New England BioLabs Co., 10 ng/μL) using mixed separation media prepared at the mixing ratios indicated above. In the displayed data, the migration time is normalized based on a high molecular weight internal standard marker for each size range (680 bp, 2720 bp, 6100 bp and 20000 bp respectively) and a low molecular weight internal standard marker common to all ranges (two vertical lines). As shown in this drawing, since the resolution was optimized for four size ranges, in the 25 bp to 500 bp range, separation was achieved between 500 bp and 517 bp, while resolution at longer chain length was incomplete. In the 100 bp to 1000 bp range, it can be seen that resolution was improved up to 1000 bp, and between 100 bp and 12000 bp, resolution was improved on the long chain side.

As the resolution serving as the criterion for sample separation, it is also possible to define a ERF (Electrophoretic response function) value comprising the allowable separation time according to the following formula (2) in addition to Rs, generate resolution maps using this ERF value as the resolution, and employ these for determination of composition of the mixed separation medium.

$$ERF = \sum_{i=1}^{k} A_i \ln \frac{R_i}{R_{id}} + B(t_M - t_L) \quad (2)$$

Here, Ri is the Rs of the ith fragment group, Rid is the target Rs, Ai is a weighting coefficient (assuming all peaks are uniform, Rs:Ai=1), $t_m$ is the maximum allowable analysis time, and $t_L$ is the experimental value of analysis time.

Next, an embodiment example of an electrophoresis device comprising a separation medium preparation device which automatically performs preparation of mixed separation media by the method described above will be described using FIG. 13.

This electrophoresis device comprises a separation medium preparation and filling mechanism 4 which has a function of preparing a separation medium and a function of filling the prepared separation medium into the separation channel of an electrophoresis chip 2 installed at a predetermined location; and an electrophoretic analysis unit 6 which has a function of applying a voltage for electrophoresis to the two ends of the separation channel of electrophoresis chip 2 and a function of measuring fluorescent light emitted from the sample. In this electrophoresis device, the separation medium preparation and filling mechanism 4, control unit 8 and computation processing unit 10 constitute the separation medium preparation device 20.

The operation of the separation medium preparation and filling mechanism 4 and electrophoretic analysis unit 6 is controlled by control unit 8. Control unit 8 controls the operation of the separation medium preparation and filling mechanism 4 and electrophoretic analysis unit 6 based on analytical parameter information received from computation processing unit 10, which is implemented for example by means of a personal computer (PC). The measurement data obtained by electrophoretic analysis unit 6 is inputted via control unit 8 into computation processing unit 10. The computation processing unit 10 comprises a data processing means 12 which performs various types of processing based on the inputted measurement data, as well as a separation medium composition determination means 14, separation medium preparation means 16 and information storage unit 18.

Information storage unit 18 stores measurement sample related information inputted by the user, information on analytical parameters, etc., and measurement data inputted via control unit 8, as well as resolution maps prepared in advance. The separation medium composition determination means 14 is configured to determine a separation medium composition and filling mechanism 4 appropriate for the measurement sample using the resolution maps stored in information storage unit 18. The separation medium preparation means 16 is configured to set the operating parameters of the separation medium composition determination means so that the composition of the separation medium will be as determined by the separation medium composition determination means 14, and issue control information based on those operating parameters to the control unit 8.

Figure 17:
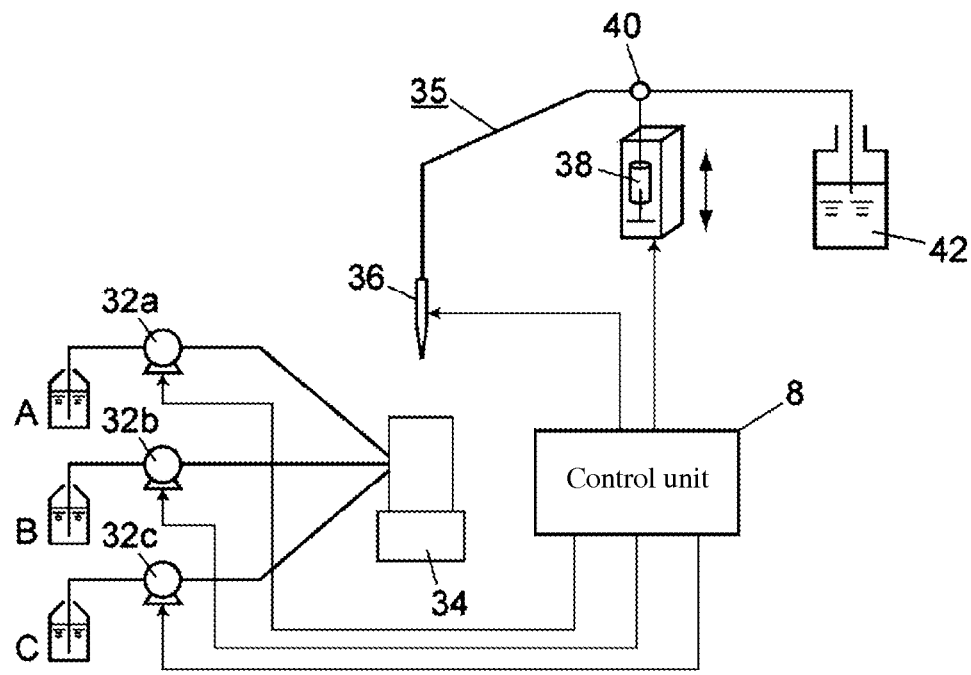
FIG. 17 is a drawing schematically illustrating an embodiment example of a separation medium preparation and filling device.
Figure 18:
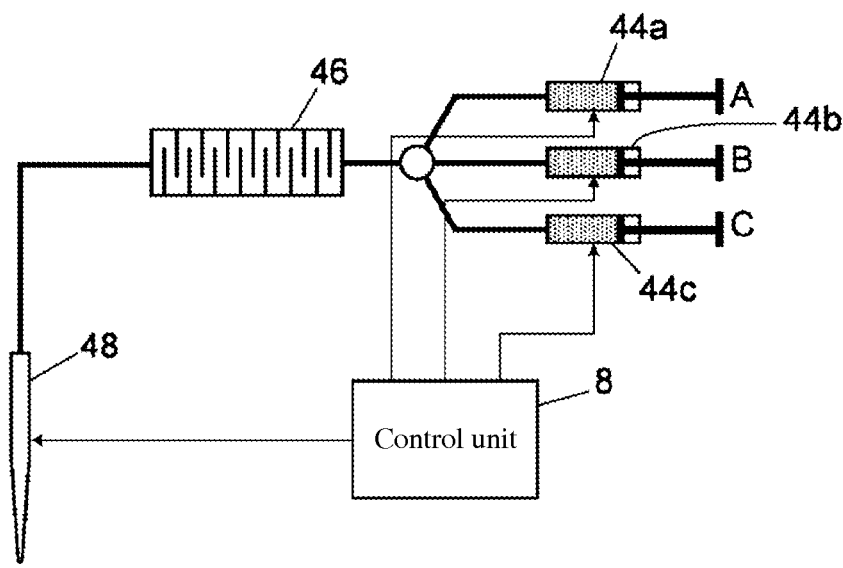
FIG. 18 is a drawing schematically illustrating another embodiment example of a separation medium preparation and filling device.

Examples of the specific configuration of separation medium preparation and filling mechanism 4 are shown in FIG. 17 and FIG. 18.

First, the example of FIG. 17 comprises a dynamic mixer 34 and performs preparation of the separation medium in the dynamic mixer 34, and is provided with liquid feed pumps 32a, 32b and 32c, which feed polymer materials A, B and C, which are different types of separation media, to the dynamic mixer 34. The liquid feed flow rates of the liquid feed pumps 32a, 32b and 32c are controlled by control unit 8 so that the mixed separation medium mixed in dynamic mixer 34 will have the composition determined by the separation medium composition determination means 14 (see FIG. 13).

The mixed separation medium prepared by mixing in the dynamic mixer 34 is filled into the separation channel of an electrophoresis chip by means of liquid dispensing mechanism 35. The liquid dispensing mechanism 35 comprises a probe 36 configured so as to be movable in the horizontal in-plane direction and vertical direction, and a syringe pump 38 which performs suction and discharge of liquid through the probe 36. The movement operation of the probe 36 and the suction and discharge operation of the syringe pump 38 are also controlled by the control unit 8. The mixed separation medium prepared in the dynamic mixer 34 is suctioned by the syringe pump 38 via the probe 36, after which the probe 36 moves to a predetermined reservoir location of the electrophoresis chip, and the mixed separation medium is filled into the separation channel by being discharged from the tip of the probe 36.

It should be noted that in the example of FIG. 17, the syringe pump 38 is configured so as to be connected to either the probe 36 or a container 42 holding a wash liquid by means of switching of a solenoid valve 40, and after the operation of filling separation medium into the separation channel, wash liquid is sucked in by the syringe pump 38 and is discharged to a predetermined waste liquid port from the probe 36, thereby allowing washing of the inner surfaces of the probe 36 to be performed.

In the example of FIG. 18, syringe pumps 44a, 44b and 44c are provided in a state where they have sucked in polymer materials A, B and C respectively, these syringe pumps 44a, 44b and 44c are connected to one end of a common static mixer 46, and the other end of the static mixer 46 is connected to the base end of the probe 48. The discharge flow rates of the syringe pumps 44a, 44b and 44c are controlled by the control unit 8 so that the composition of the mixed separation medium prepared by mixing in the static mixer 46 will be the composition determined by the separation medium composition determination means 14 (see FIG. 13). The probe 48 can move in the horizontal in-plane direction and vertical direction, and its operation is controlled by the control unit 8.

Figure 13:
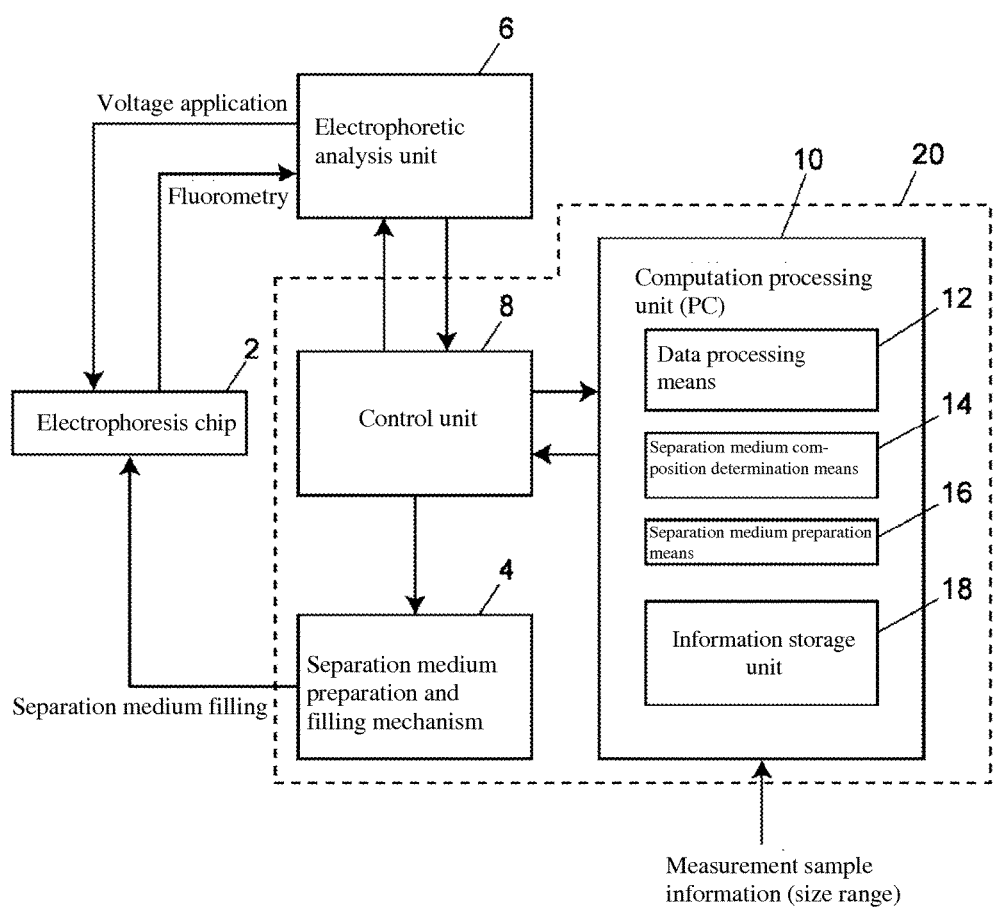
FIG. 13 is a block diagram schematically illustrating an example of the constitution of an electrophoretic analysis device comprising a separation medium preparation and filling device.
Figure 14:
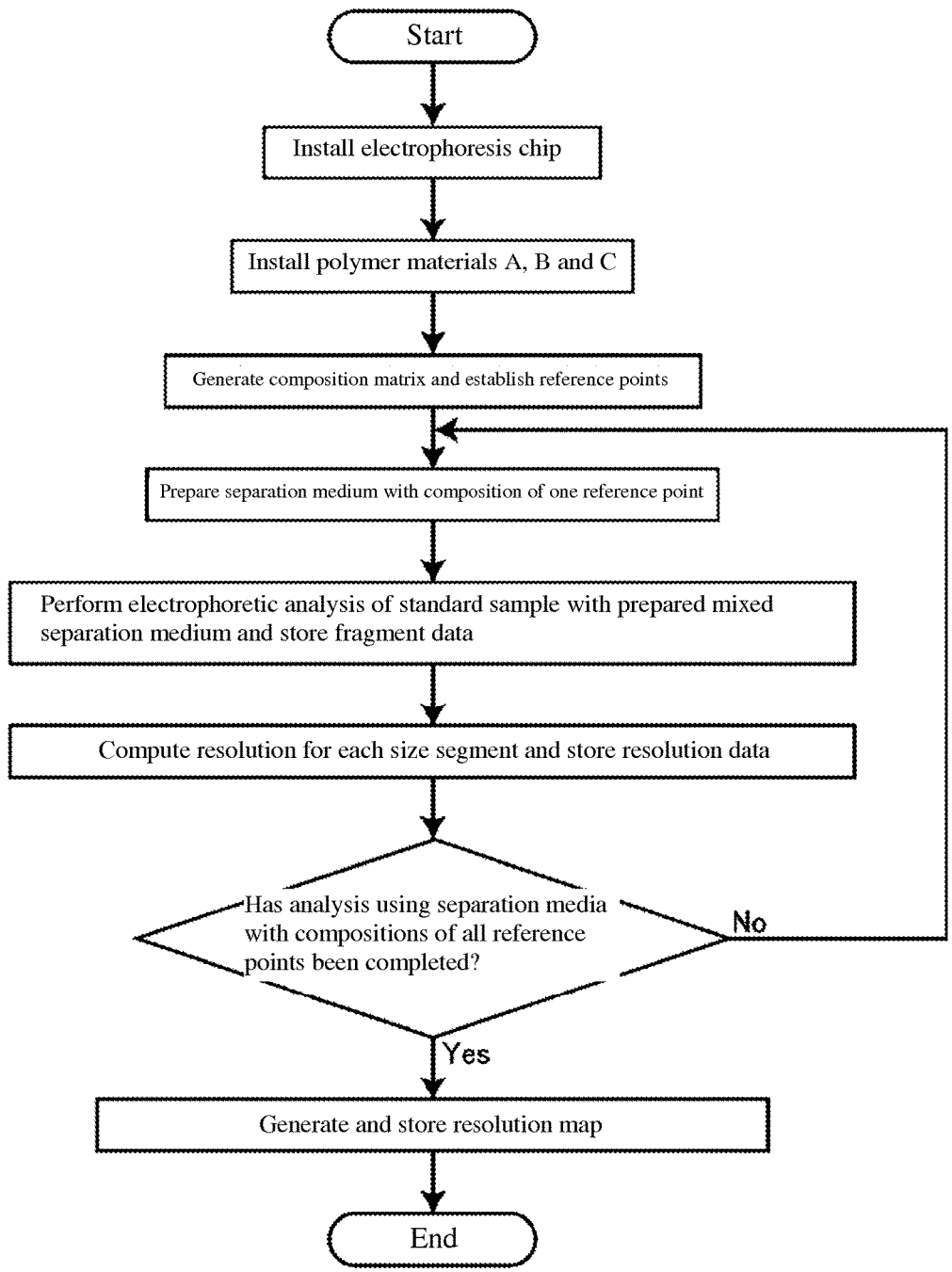
FIG. 14 is a flow chart illustrating an example of the procedure for generating resolution maps using the electrophoretic analysis device of the same embodiment example.

An example of the method of generating a resolution map for use in determining the composition of a mixed separation medium using the electrophoresis device of FIG. 13 will be described using the flow chart of FIG. 14.

First, electrophoresis chip 2 and containers holding three types of polymer materials A, B and C are installed in the device. A composition matrix as shown in FIG. 3 is generated, and reference points are established on that composition matrix. The generation of the composition matrix and the establishment of reference points may also be done automatically by the computation processing unit 10 according to the number of polymer materials (separation media) inputted by the user. Furthermore, composition matrix and reference point information may be provided in advance in the information storage unit 18.

The following operations are performed sequentially on all the reference points on the composition matrix.

A mixed separation medium of the composition corresponding to the given reference point is prepared, and electrophoretic analysis is performed on a standard sample with the prepared mixed separation medium. The fragment data obtained through this electrophoretic analysis is stored in information storage unit 18. Data processing means 12 computes the resolution for each size segment delimited by the fragments in the fragment data, and stores the resulting resolution data in information storage unit 18.

Data as shown in FIG. 5 is obtained by performing the above operation on all the reference points, and based on this data, the resolution at each reference point of each size segment is mapped onto the composition matrix to generate resolution maps as shown in FIG. 6 through FIG. 9. The generated resolution maps are stored in information storage unit 18.

Figure 16:
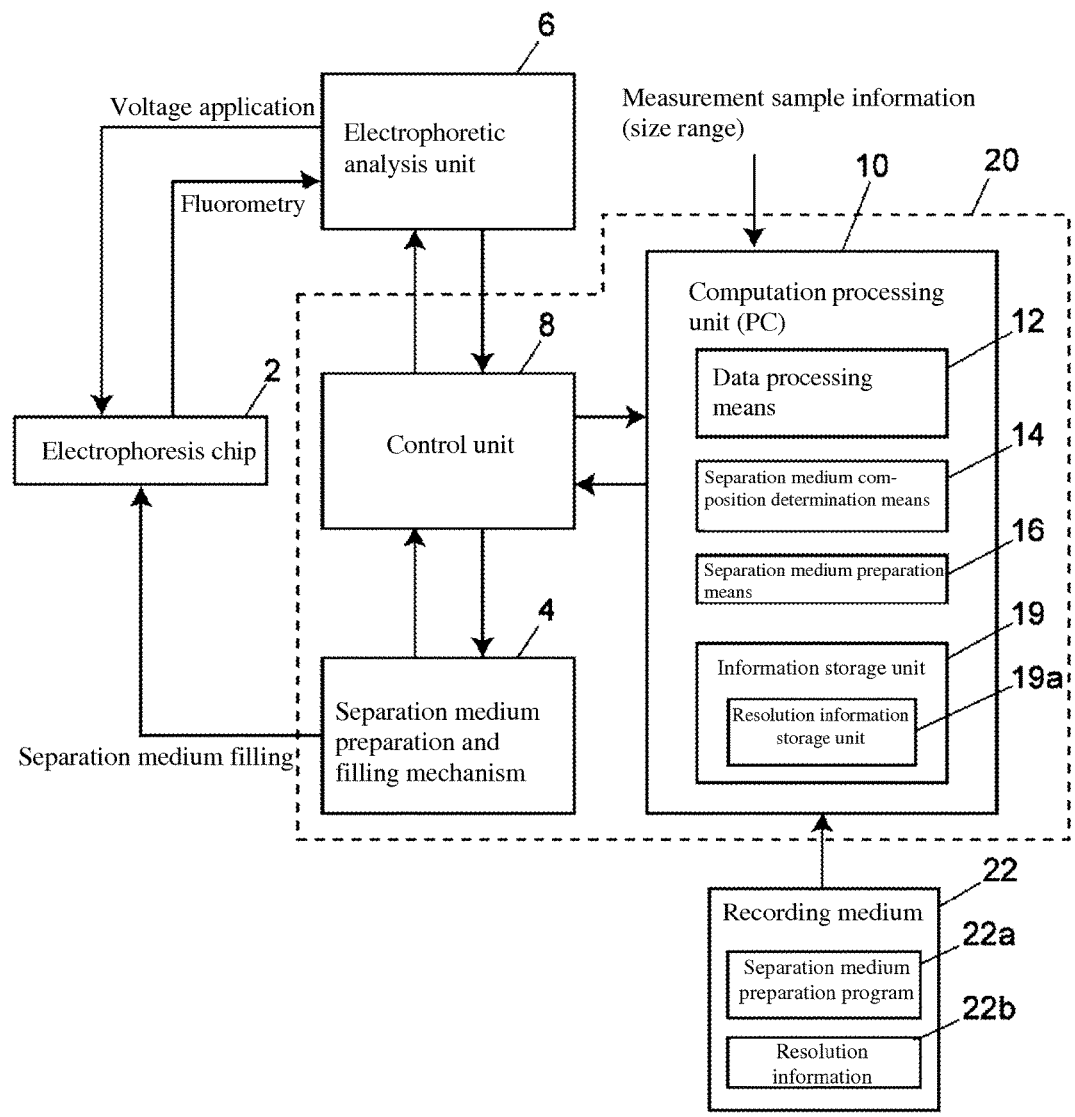
FIG. 16 is a block diagram schematically illustrating another example of the constitution of an electrophoretic analysis device comprising a separation medium preparation and filling unit.

The generation and storage of resolution maps described above need not necessarily be performed by the user of the electrophoresis device. As shown in FIG. 16, by determining the compositions of separation medium using resolution maps and providing in advance a recording medium 22 comprising a CD (compact disc) or the like which holds a separation medium preparation program 22a for preparing separation media of those compositions along with resolution maps and other resolution information 22b, this function and information can be installed from the recording medium 22 into the computation processing unit 10, thereby making it possible to provide the computation processing unit 10 with a separation medium composition determination means 14, a separation medium preparation means 16 and a separation information storage unit 19a.

Figure 15:
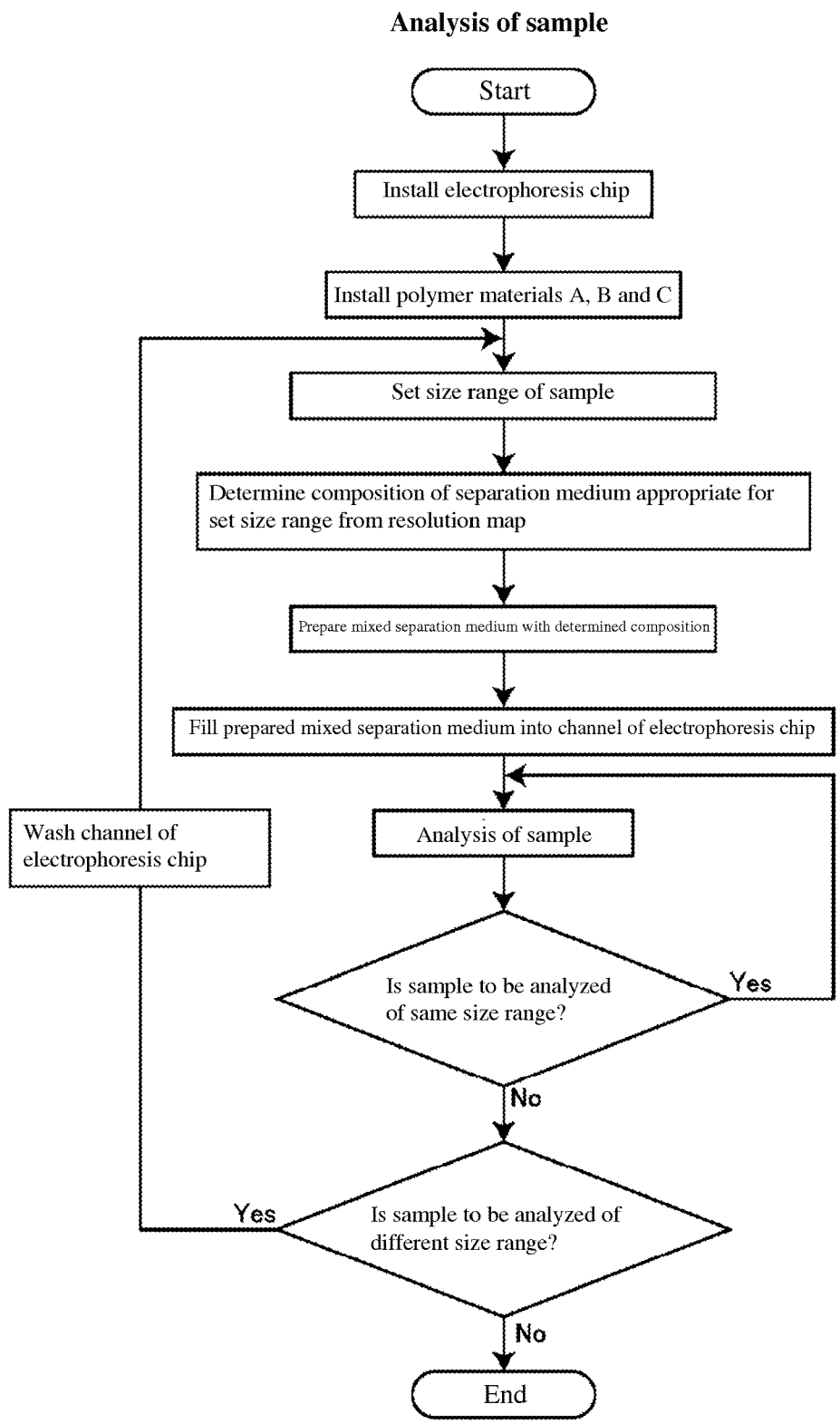
FIG. 15 is a flow chart showing an example of the sample analysis procedure performed by the electrophoresis analysis device of the same embodiment example.

An example of the sample analysis method using the electrophoresis device in the state where resolution maps have been stored in information storage unit 18 will be described using FIG. 15.

After installing the electrophoresis chip 2 and containers holding polymer materials A, B and C in the device, the user sets the sample size range in the computation processing unit 10, whereupon the separation medium composition determination means 14 retrieves the resolution maps corresponding to the set size range from the information storage unit 18, sets a resolution threshold value (for example, Rs>1) for those maps, and extracts a high resolution region, thereby determining the composition of the mixed separation medium appropriate for that size range.

Separation medium preparation means 16 sets the operating parameters of the separation medium preparation and filling mechanism 4 required for making the determined composition and issues the corresponding information to the control unit 8, whereupon the separation medium preparation and filling mechanism 4 mixes the polymer materials A, B and C at the corresponding mixing ratio to prepare a mixed separation medium and fills it into the separation channel of the electrophoresis chip 2. The sample then enters the sample reservoir of the electrophoresis chip and voltage is applied to the two ends of the separation channel by the electrophoretic analysis unit 6, whereby electrophoretic analysis of the sample is performed.

After electrophoretic analysis of the sample has been completed, to next perform analysis of a sample of the same size range, the same separation medium is used to perform electrophoretic analysis of the next sample. On the other hand, to next perform analysis of a sample of a different size range, washing of the separation channel is performed, after which the composition of the separation medium appropriate for the next sample size range set by the user is determined, a mixed separation medium is prepared and filling with the prepared separation medium is performed in sequence, after which electrophoretic analysis is carried out.

Figure 19:
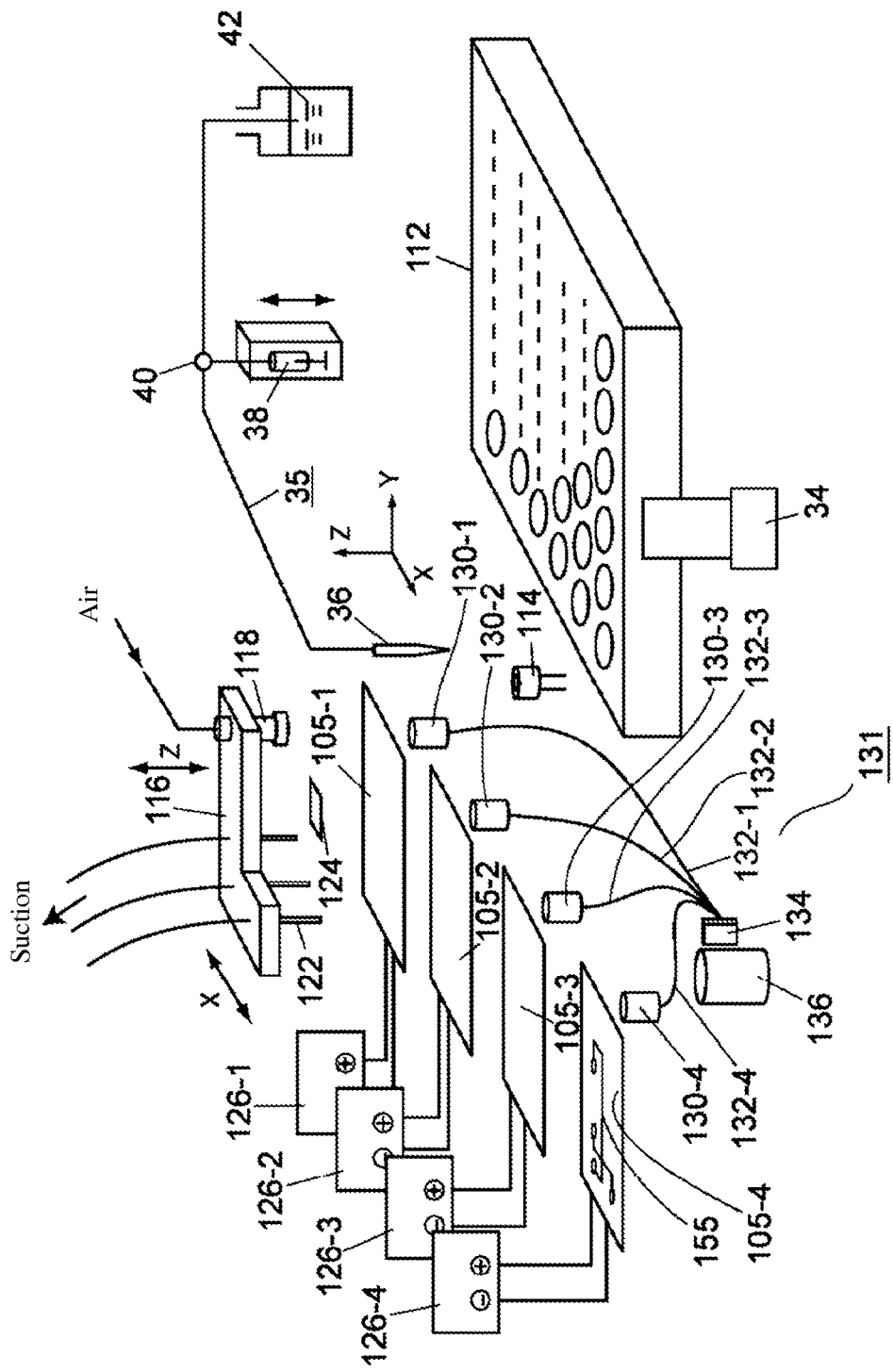
FIG. 19 is a drawing schematically illustrating an embodiment example of a microchip electrophoresis device.

The major parts of a microchip electrophoresis device are shown in FIG. 19. This electrophoresis device comprises a separation medium preparation device having the configuration of FIG. 17 and prepares a separation medium having separation characteristics appropriate for the size range of the sample and fills it into the separation channel of the microchip. In this example, the dynamic mixer of FIG. 17 is used as the mechanism for preparing the separation medium, but the static mixer of FIG. 18 may be used as well.

Four microchips 105-1 through 105-4 are held in a retention unit (not illustrated) as the electrophoresis chip. The microchips 105-1 through 105-4 each have a single separation channel formed for processing one sample.

Dispensing unit 35 for dispensing separation medium and sample into the microchips 105-1 through 105-4 is provided with a syringe pump 38 which performs suction and discharge, a probe 36 comprising a dispensing nozzle and a wash water container 42, and the probe 36 and wash water container 42 are connected to the syringe pump 38 via a three-way solenoid valve 40. The sample is held in wells on a microtiter plate 112 and is dispensed by the dispensing unit 35 into microchips 105-1 through 105-4. The separation medium is prepared in dynamic mixer 34 according to the size range of the sample and is sucked in by the probe 36 and dispensed into the reservoir at one end of the separation channel of one of the microchips 105-1 through 105-4. 114 is a washing unit for washing the probe 36 and overflows with wash water.

Dispensing unit 35 connects the three-way solenoid valve 40 in the direction in which the probe 36 and syringe pump 38 will be connected, sucks the separation medium or sample into the probe 36, and discharges it into the separation channel of one of the microchips 105-1 through 105-4 using the syringe pump 38. When washing the probe 36, the three-way solenoid valve 40 is switched in the direction which will connect the syringe pump 38 and wash water container 42, sucks water into the syringe pump 38, and then immerses the probe 36 into the water of washing unit 114, switches the three-way solenoid valve 40 to the side which connects the syringe pump 38 and probe 36, and performs washing by discharging wash water from inside the probe 36.

To fill the separation medium which has been dispensed into the reservoir at one end of the separation channel of microchips 105-1 through 105-4 into the channel, the four microchips 105-1 through 105-4 are provided with a common buffer filling and evacuation unit 116. The buffer filling and evacuation unit 116 presses an air discharge port 118 over the reservoir at one end of the separation channel of one of the microchips 105-1 through 105-4 so as to maintain air-tightness, inserts suction nozzles 122 into the other reservoirs, blows air through the air discharge port 118 so as to push the separation medium into the separation channel, and evacuates the separation medium which overflows from the other reservoirs to the outside through nozzles 122 by means of suction pump 123.

To independently apply voltage for electrophoresis to each of the microchips 105-1 through 105-4, each of the microchips 105-1 through 105-4 is provided with an independent electrophoresis high voltage power supply 126 (126-1 through 126-4).

A fluorometry unit 131 for detecting sample components electrophoretically separated in the separation channels 155 of the microchips 105-1 through 105-4 is provided for each of the microchips 105-1 through 105-4 and comprises LEDs (light emitting diodes) 130-1 through 130-4 which irradiate a portion of the respective separation channel with excitation light; optical fibers 132-1 through 132-4 which receive fluorescent light emitted when the sample components moving through the separation channels are excited by the excitation light from the LEDs 130-1 through 130-4; and a photomultiplier tube 136 which receives fluorescent light through a filter 134 that removes the excitation light component from the fluorescent light coming from the optical fibers 132-1 through 132-4 and transmits only the fluorescent light component. By causing the LEDs 130-1 through 130-4 to emit light at staggered times, four fluorescent lights can be discriminated and detected with a single photomultiplier tube 136.

DESCRIPTION OF REFERENCE SYMBOLS

2 Electrophoresis chip
4 Separation medium preparation and filling mechanism
6 Electrophoretic analysis unit
8 Control unit
10 Computation processing unit
12 Data processing means
14 Separation medium composition determination means
16 Separation medium preparation means
18, 19 Information storage unit
19*a* Resolution information storage unit
20 Recording medium
22*a* Separation medium preparation program
22*b* Resolution information

What is claimed:

1. A method of determining a composition of a separation medium for electrophoresis wherein the separation medium to be used for electrophoretic analysis of a measurement sample is determined by performing the following steps in the indicated sequence:
   preparing, with a processor, resolution maps for each of multiple contiguous size segments, the resolution maps each including multiple mixture combinations of two or three types of separation media, wherein each mixture combination includes a specific amount of each of the two or three types of separation media, and wherein the resolution maps show, based on a location on each surface, a relationship between a composition of a mixed separation medium prepared by mixing at least one of the two or three types of separation media and a resolution obtained by performing analysis using a separation medium of that composition;
   extracting, with the processor, a high resolution region having the resolution necessary for separation of the measurement sample by extracting a region of a predetermined resolution or higher, from a resolution map of the size segment to which a size range of the measurement sample extends; and
   a mixed separation medium composition determination step comprising selecting, with the processor, a point within said high resolution region as a high resolution point and determining the composition of the high resolution point as the composition of the mixed separation medium to be used for electrophoretic analysis of the measurement sample.

2. The method of determining the composition of a separation medium for electrophoresis as described in claim 1, wherein, when the size range of the measurement sample extends over multiple said size segments,
   in said extracting step, said high resolution region is extracted from each of the resolution maps of those size segments, and a region contained within all of said high resolution regions is extracted as a high resolution overlap region; and
   in said mixed separation medium composition determination step, a point within said high resolution overlap region is selected as a high resolution point, and the composition of the high resolution point is determined as the composition of the mixed separation medium to be used for electrophoretic analysis of the measurement sample.

3. An electrophoresis method comprising:
   determining the composition of a separation medium for electrophoresis by the method of claim 2;
   filling a separation channel of an electrophoresis chip with the separation medium;
   dispensing a sample into a sample reservoir provided at one end of said separation channel; and
   causing the sample to migrate through said separation channel by applying a voltage between two ends of said separation channel and detecting migrating components of said sample at a predetermined location of said separation channel.

4. An electrophoresis method comprising:
   determining the composition of a separation medium for electrophoresis by the method of claim 1;
   filling a separation channel of an electrophoresis chip with the separation medium;
   dispensing a sample into a sample reservoir provided at one end of said separation channel; and
   causing the sample to migrate through said separation channel by applying a voltage between two ends of said separation channel and detecting migrating components of said sample at a predetermined location of said separation channel.

5. The method according to claim 1, wherein an electrophoretic response function (ERF) value is defined by an ERF equation:

$$ERF = \sum_{i=1}^{k} A_i \ln\frac{R_i}{R_{id}} + B(t_M - t_L) \qquad (2)$$

and preparing the resolution maps comprises calculating the ERF value by the ERF equation.

6. A computer readable medium including a program for determining a composition of a separation medium for electrophoresis, configured so as to determine the composition of the separation medium to be used for electrophoretic analysis of a measurement sample by executing the following steps in the indicated sequence,
preparing resolution maps for each of multiple contiguous size segments, the resolution maps each including multiple mixture combinations of two or three types of separation media, wherein each mixture combination includes a specific amount of each of the two or three types of separation media, wherein the resolution maps show a relationship between a composition of a mixed separation medium prepared by mixing at least one of the two or three types of separation media and a resolution obtained by performing analysis using a separation medium of that composition based on location on a surface thereof;
a high resolution region extraction step wherein a high resolution region having the resolution necessary for separation of the measurement sample is extracted, by extracting a region of a predetermined resolution or higher, from a resolution map of the size segment to which a size range of the measurement sample extends; and
a mixed separation medium composition determination step wherein a point within said high resolution region is selected as a high resolution point and the composition of the high resolution point is determined as the composition of the mixed separation medium to be used for electrophoretic analysis of the measurement sample.

7. The computer readable medium including the program for determining the composition of a separation medium for electrophoresis as described in claim 6, wherein, when the size range of the measurement sample extends over multiple said size segments,
in said high resolution region extraction step, said high resolution region is extracted from each of the resolution maps of those size segments, and a region contained within all of said high resolution regions is extracted as a high resolution overlap region; and
in said mixed separation medium composition determination step, a point within said high resolution overlap region is selected as a high resolution point, and the composition of the high resolution point is determined as the composition of the mixed separation medium to be used for electrophoretic analysis of the measurement sample.

8. The computer readable medium including the program for determining the composition of a separation medium for electrophoresis as described in claim 6, wherein an electrophoretic response function (ERF) value is defined by an ERF equation:

$$ERF = \sum_{i=1}^{k} A_i \ln\frac{R_i}{R_{id}} + B(t_M - t_L) \qquad (2)$$

and preparing the resolution maps comprises calculating the ERF value by the ERF equation.

9. A separation medium preparation device comprising:
a pump array which individually feeds multiple types of separation medium liquids;
a mixer for mixing the separation medium liquids fed by said pump array;
a resolution map information storage which stores resolution map information comprising resolution maps, which show a relationship between the composition of a mixed separation medium prepared by mixing multiple types of separation media and the resolution obtained by performing analysis using a separation medium of that composition based on location on a surface thereof, and are prepared for each of multiple contiguous size segments;
a computer readable medium including a program for determining a composition of a separation medium for electrophoresis, configured so as to determine the composition of the separation medium to be used for electrophoretic analysis of a measurement sample by executing the following steps in the indicated sequence,
preparing resolution maps, which show a relationship between a composition of a mixed separation medium prepared by mixing multiple types of separation media and the resolution obtained by performing analysis using a separation medium of that composition based on location on a surface thereof, wherein the resolution maps are prepared for each of multiple contiguous size segments:
a high resolution region extraction step wherein a high resolution region having the resolution necessary for separation of the measurement sample is extracted from the resolution map of the size segment to which a size range of the measurement sample extends; and
a mixed separation medium composition determination step wherein a point within said high resolution region is selected as a high resolution point and the composition of the high resolution point is determined as the composition of the mixed separation medium to be used for electrophoretic analysis of the measurement sample,
a controller that determines the composition of the separation medium by means of said program on the basis of a set measurement sample size range, and controls operation of said pump array to prepare a mixed separation medium so as to have the determined composition.

10. The separation medium preparation device as described in claim 9, wherein said pump array comprises three syringe pumps for feeding each separation medium liquid;
a static mixer whereof one end is connected to all of the syringe pumps, and which mixes the separation medium liquids fed by said syringe pumps; and a probe which is connected to the other end of said static mixer and dispenses the mixed separation medium prepared by mixing in said static mixer.

11. A separation medium preparation device as described in claim 10, wherein said resolution map information and composition determination program are inputted via a recording medium.

12. A separation medium preparation device as described in claim 9, wherein said resolution map information and composition determination program are inputted via a recording medium.

13. The separation medium preparation device according to claim 9, wherein an electrophoretic response function (ERF) value is defined by an ERF equation:

$$ERF = \sum_{i=1}^{k} A_i \ln \frac{R_i}{R_{id}} + B(t_M - t_L) \quad (2)$$

and preparing the resolution maps comprises calculating the ERF value by the ERF equation.

14. A separation medium preparation device comprising:
a pump array which individually feeds multiple types of separation medium liquids;
a mixer for mixing the separation medium liquids fed by said pump array;
a resolution map information storage which stores resolution map information comprising resolution maps, which show a relationship between the composition of a mixed separation medium prepared by mixing multiple types of separation media and a resolution obtained by performing analysis using a separation medium of that composition based on location on a surface thereof, and wherein the resolution maps are prepared for each of multiple contiguous size segments;
a computer readable medium including a program for determining a composition of a separation medium for electrophoresis, configured so as to determine the composition of the separation medium to be used for electrophoretic analysis of a measurement sample by executing the following steps in the indicated sequence,
preparing resolution maps, which show a relationship between a composition of a mixed separation medium prepared by mixing multiple types of separation media and the resolution obtained by performing analysis using a separation medium of that composition based on location on a surface thereof, wherein the resolution maps are prepared for each of multiple contiguous size segments:
a high resolution region extraction step wherein a high resolution region having the resolution necessary for separation of the measurement sample is extracted from the resolution map of the size segment to which a size range of the measurement sample extends; and
a mixed separation medium composition determination step wherein a point within said high resolution region is selected as a high resolution point and the composition of the high resolution point is determined as the composition of the mixed separation medium to be used for electrophoretic analysis of the measurement sample,
wherein, when the size range of the measurement sample extends over multiple said size segments, in said high resolution region extraction step, said high resolution region is extracted from each of the resolution maps of those size segments, and a region contained within all of said high resolution regions is extracted as a high resolution overlap region; and
in said mixed separation medium composition determination step, a point within said high resolution overlap region is selected as a high resolution point, and the composition of the high resolution point is determined as the composition of the mixed separation medium to be used for electrophoretic analysis of the measurement sample,
a controller that determines the composition of the separation medium by means of said program on the basis of a set measurement sample size range, and controls operation of said pump array to prepare a mixed separation medium so as to have the determined composition.

15. The separation medium preparation device as described in claim 14, wherein said pump array comprises three syringe pumps for feeding each separation medium liquid;
a static mixer whereof one end is connected to all of the syringe pumps, and which mixes the separation medium liquids fed by said syringe pumps; and
a probe which is connected to the other end of said static mixer and dispenses the mixed separation medium prepared by mixing in said static mixer.

16. A separation medium preparation device as described in claim 15, wherein said resolution map information and composition determination program are inputted via a recording medium.

17. A separation medium preparation device as described in claim 14, wherein said resolution map information and composition determination program are inputted via a recording medium.

18. The separation medium preparation device according to claim 14, wherein an electrophoretic response function (ERF) value is defined by an ERF equation:

$$ERF = \sum_{i=1}^{k} A_i \ln \frac{R_i}{R_{id}} + B(t_M - t_L) \quad (2)$$

and preparing the resolution maps comprises calculating the ERF value by the ERF equation.

19. A separation medium preparation device comprising:
a pump array which individually feeds multiple types of separation medium liquids;
a mixer for mixing the separation medium liquids fed by said pump array;
a resolution map information storage which stores resolution map information comprising resolution maps, which show a relationship between the composition of a mixed separation medium prepared by mixing multiple types of separation media and the resolution obtained by performing analysis using a separation medium of that composition based on location on a surface thereof, and are prepared for each of multiple contiguous size segments;
a computer readable medium including a program for determining a composition of a separation medium for electrophoresis, configured so as to determine the composition of the separation medium to be used for electrophoretic analysis of a measurement sample by executing the following steps in the indicated sequence, preparing resolution maps including multiple mixture combinations of two or three types of separation media, wherein each mixture combination includes a specific amount of each of the two or three types of separation media, wherein the resolution maps show a relationship between a composition of a mixed separation medium prepared by mixing at least one of the two or three types of separation media and a resolution obtained by performing analysis using a separation medium of that composition based on location on a surface thereof, wherein the resolution maps are prepared for each of multiple contiguous size segments:

a high resolution region extraction step wherein a high resolution region having the resolution necessary for separation of the measurement sample is extracted, by extracting a region of a set resolution or higher, from the resolution map of the size segment to which a size range of the measurement sample extends; and a mixed separation medium composition determination step wherein a point within said high resolution region is selected as a high resolution point and the composition of the high resolution point is determined as the composition of the mixed separation medium to be used for electrophoretic analysis of the measurement sample, a controller that determines the composition of the separation medium by means of said program on the basis of a set measurement sample size range, and controls operation of said pump array to prepare a mixed separation medium so as to have the determined composition.

\* \* \* \* \*